US010971267B2

(12) United States Patent
Weschler et al.

(10) Patent No.: US 10,971,267 B2
(45) Date of Patent: Apr. 6, 2021

(54) SYSTEMS AND METHODS FOR AGGREGATION OF AUTOMATICALLY GENERATED LABORATORY TEST RESULTS

(71) Applicant: Medial Research Ltd., Kfar-Malal (IL)

(72) Inventors: Arturo Weschler, Kfar-Saba (IL); Nir Kalkstein, Herzlia (IL)

(73) Assignee: Medial Research Ltd., Kfar Malal (IL)

( * ) Notice: Subject to any disclaimer, the term of this patent is extended or adjusted under 35 U.S.C. 154(b) by 268 days.

(21) Appl. No.: 15/979,495

(22) Filed: May 15, 2018

(65) Prior Publication Data

US 2018/0330819 A1 Nov. 15, 2018

Related U.S. Application Data

(60) Provisional application No. 62/506,038, filed on May 15, 2017.

(51) Int. Cl.
*G16H 40/67* (2018.01)
*G16H 10/40* (2018.01)
(Continued)

(52) U.S. Cl.
CPC ............ *G16H 40/67* (2018.01); *G16B 50/00* (2019.02); *G16H 10/40* (2018.01); *G16H 10/60* (2018.01); *G16H 50/20* (2018.01)

(58) Field of Classification Search
CPC ........ G16H 10/60; G16H 50/20; G16H 40/20; G16H 40/63; G16H 80/00; G16H 40/67;
(Continued)

(56) References Cited

U.S. PATENT DOCUMENTS

2005/0055240 A1* 3/2005 Walsh .................... G06Q 50/22
705/2
2005/0209785 A1* 9/2005 Wells ..................... G16H 50/20
702/19
(Continued)

FOREIGN PATENT DOCUMENTS

EP 1147423 10/2001
WO WO 00/46603 8/2000

OTHER PUBLICATIONS

European Search Report and the European Search Opinion Dated Sep. 18, 2018 From the European Patent Office Re. Application No. 18172436.0. (10 Pages).

*Primary Examiner* — Elaine Gort
*Assistant Examiner* — Shyam M Goswami (57) ABSTRACT

There is provided a method of computing computed pathological indication(s), comprising: receiving an indication of values of current laboratory test results calculated based on an automated analysis of laboratory sample(s) collected from a target individual, selecting classifier(s) according to an analysis of the indication of values of the current laboratory test results, determining additional laboratory test(s) according to the analysis of the indication of values of the current laboratory test results and/or the selected classifier(s), generating instructions for automatic execution of second automatic laboratory testing device(s) on the laboratory sample(s) to obtain a second indication of a second value of the additional laboratory test(s), and evaluating computed pathological indication(s) by applying the selected classifier(s) to the indication of values of the current laboratory test results and the second indication of the second value of the additional laboratory test result(s).

27 Claims, 5 Drawing Sheets

(51) Int. Cl.
   *G16H 10/60*   (2018.01)
   *G16H 50/20*   (2018.01)
   *G16B 50/00*   (2019.01)

(58) Field of Classification Search
   CPC ........ G16H 50/30; G16H 20/00; G16H 20/40; G16H 40/40; G16H 10/40; H04L 67/10; H04L 29/08; H04L 12/24; G06F 19/30; G06F 19/32; G06F 19/34; G06F 19/36; G06F 3/0484; G06F 19/00; G06Q 50/22; G06Q 50/24; A61B 5/00; A61B 5/145; A61B 5/14552; A61B 5/02; A61B 5/14542; A61B 5/7475; A61B 5/742; A61B 5/14546; A61B 5/01; A61B 5/0022; A61B 5/746; A61B 2560/0271; A61B 5/4848; A61B 2017/00809; G16B 50/00
   See application file for complete search history.

(56) References Cited

U.S. PATENT DOCUMENTS

| | | | |
|---|---|---|---|
| 2010/0174505 A1* | 7/2010 | Abraham-Fuchs | G16H 10/60 702/108 |
| 2012/0123686 A1 | 5/2012 | Xiang et al. | |
| 2015/0012300 A1* | 1/2015 | Smith | G16H 40/20 705/3 |
| 2015/0193583 A1* | 7/2015 | McNair | G16H 50/20 705/2 |
| 2016/0232310 A1* | 8/2016 | Dunn | G06Q 30/04 |
| 2019/0242894 A1* | 8/2019 | Oved | G01N 33/56911 |

* cited by examiner

SYSTEMS AND METHODS FOR AGGREGATION OF AUTOMATICALLY GENERATED LABORATORY TEST RESULTS

RELATED APPLICATION

This application claims the benefit of priority under 35 USC § 119(e) of U.S. Provisional Patent Application No. 62/506,038 filed on May 15, 2017, the contents of which are incorporated herein by reference in their entirety.

BACKGROUND OF THE INVENTION

The present invention, in some embodiments thereof, relates to systems and methods for analyzing laboratory tests and, more specifically, but not exclusively, to systems and methods for enhancing laboratory testing.

A laboratory information system (LIS) is an information management system that manages automated laboratory testing equipment, and stores the generated test results in a database.

SUMMARY OF THE INVENTION

According to a first aspect, a method of providing a client terminal with at least one computed pathological indication in response to an indication of current laboratory test results of a patient, comprises: receiving by a computing system associated with a database storing a plurality of classifiers, from at least one automated laboratory testing device and via a network, an indication of values of a plurality of current laboratory test results calculated based on an automated analysis of at least one laboratory sample collected from a target individual, selecting at least one classifier from the plurality of classifiers according to an analysis of the indication of values of the plurality of current laboratory test results, determining at least one additional laboratory test according to at least one of: the analysis of the indication of values of the plurality of current laboratory test results and the selected at least one classifier, generating instructions for automatic execution of at least one second automatic laboratory testing device on the at least one laboratory sample to obtain a second indication of a second value of the at least one additional laboratory test, evaluating at least one computed pathological indication by applying the selected at least one classifier to the indication of values of the plurality of current laboratory test results and the second indication of the second value of the at least one additional laboratory test result, and outputting the value of the at least one computed pathological indication for presentation by the client terminal.

According to a second aspect, a system for providing a client terminal with at least one computed pathological indication in response to an indication of current laboratory test results of a patient, comprises: a non-transitory memory having stored thereon a code for execution by at least one hardware processor of a computing device associated with a database storing a plurality of classifiers and associated with at least one automated laboratory testing device via a network, the code comprising: code for receiving an indication of values of a plurality of current laboratory test results calculated based on an automated analysis of at least one laboratory sample collected from a target individual, code for selecting at least one classifier from the plurality of classifiers according to an analysis of the indication of values of the plurality of current laboratory test results, code for determining at least one additional laboratory test according to at least one of: the analysis of the indication of values of the plurality of current laboratory test results and the selected at least one classifier, code for generating instructions for automatic execution of at least one second automatic laboratory testing device on the at least one laboratory sample to obtain a second indication of a second value of the at least one additional laboratory test, code for evaluating at least one computed pathological indication by applying the selected at least one classifier to the indication of values of the plurality of current laboratory test results and the second indication of the second value of the at least one additional laboratory test result, and code for outputting the value of the at least one computed pathological indication for presentation by the client terminal.

According to a third aspect, a computer program product for providing a client terminal with at least one computed pathological indication in response to an indication of current laboratory test results of a patient, comprises: a non-transitory memory having stored thereon a code for execution by at least one hardware processor of a computing device associated with a database storing a plurality of classifiers and associated with at least one automated laboratory testing device via a network, the code comprising: instructions for receiving an indication of values of a plurality of current laboratory test results calculated based on an automated analysis of at least one laboratory sample collected from a target individual, instructions for selecting at least one classifier from the plurality of classifiers according to an analysis of the indication of values of the plurality of current laboratory test results, instructions for determining at least one additional laboratory test according to at least one of: the analysis of the indication of values of the plurality of current laboratory test results and the selected at least one classifier, instructions for generating instructions for automatic execution of at least one second automatic laboratory testing device on the at least one laboratory sample to obtain a second indication of a second value of the at least one additional laboratory test, instructions for evaluating at least one computed pathological indication by applying the selected at least one classifier to the indication of values of the plurality of current laboratory test results and the second indication of the second value of the at least one additional laboratory test result, and instructions for outputting the value of the at least one computed pathological indication for presentation by the client terminal.

The systems and/or methods and/or code instructions described herein provide a technical solution to the technical problem of analyzing multiple individual laboratory test results to obtain an overall indication of the patient. In particular, the technical problem relates to aggregating the multiple individual laboratory test results in an object manner to obtain an overall objective measure indicative of the state of the patient and/or predicting a future state of the patient.

For example, current liver function or a prediction of liver failure may be obtained by the following tests: AST, ALT, AST/ALT, aPTT, albumin, bilirubin (direct and indirect), history of alcohol consumption, history of use of hepatotoxic substances, and presence of ascites. The clinician subjectively and manually integrates the test results in their head based on clinical experience, to estimate the severity of liver injury. Monitoring improvement or degradation in the condition of the patient by repeating the multiple tests is difficult and subjective.

Moreover, analysis of multiple test results, in particular changes between values over tests conducted over multiple periods of time, is difficult. A situation that is especially challenging arises when the values of the test results fall within normal ranges, but a pattern of multiple tests results, and/or a trend and/or velocity in change of values over time may be indicative of the existence or developing medical problem that is otherwise hidden. Moreover, tests that would otherwise seem clinically irrelevant in isolation may not be requested by the clinician, for example, when the clinician is unable to appreciate the significant of the additional test in combination with the standard set of tests usually ordered for evaluation of the clinical indication.

The systems and/or methods and/or code instructions described herein utilize currently obtained laboratory sample(s) in the current round of automated laboratory tests to compute the computed pathological indication(s), which reduces or prevents additional future automated testing cycles that might otherwise arise, for example, by the treating physician ordering another set of tests that are performed during another round of automated testing. The testing efficiency of the automated laboratory testing equipment is improved.

In a further implementation form of the first, second, and third aspects, the at least one additional laboratory test is not included in the plurality of current laboratory tests received in an originating request from a user.

In a further implementation form of the first, second, and third aspects, each of the plurality of classifiers computes a respective computed pathological indication from a subset of current laboratory test results to generate a clinical indication of at least one of: normal biological processes, pathogenic processes, and pharmacological responses to a therapeutic intervention.

In a further implementation form of the first, second, and third aspects, the at least one computed pathological indication denotes an aggregation of the respective subset of current laboratory test results, wherein at least one member of the subset of current laboratory test results is statistically insignificantly correlated with the clinical indication denoted by the evaluated at least one computed pathological indication.

In a further implementation form of the first, second, and third aspects, the at least one second automatic laboratory testing device executes the at least one additional laboratory test according to the generated instructions on at least a portion of the at least one laboratory sample tested by the automatic laboratory testing device.

In a further implementation form of the first, second, and third aspects, the method further comprises and/or the processor is further configured to and/or the computer program product includes additional instructions for determining according to an analysis of the indication of values of the plurality of current laboratory test results, at least one additional patient parameter of the target individual for application of the selected at least one classifier, accessing a clinical data repository database to obtain an indication of a value of at least one additional patient parameter of the target individual, and applying the selected at least one classifier to the indication of the values of the plurality of current laboratory test results and the at least one additional patient parameter.

In a further implementation form of the first, second, and third aspects, the at least one additional patient parameter is selected from the group consisting of: a previous measurement of at least one of the plurality of current laboratory test results, a demographic parameter, a medical diagnosis, a smoking parameter, a medication use parameter, a family history parameter, a genetic parameter, a medical history parameter, and a physical exam finding parameter.

In a further implementation form of the first, second, and third aspects, the method further comprises and/or the processor is further configured to and/or the computer program product includes additional instructions for computing a change in the value of at least one of the plurality of current laboratory test results and at least one previous value of the at least one of the plurality of current laboratory test results, and applying the selected at least one classifier to the computed change in the value. In a further implementation form of the first, second, and third aspects, the method further comprises and/or the processor is further configured to and/or the computer program product includes additional instructions for analyzing the value of the at least one computed pathological indication according to a set-of-rules in view of the indication of values of the plurality of current laboratory test results to detect an aberration from an expected value of the at least one computed pathological indication, and generating an alert on a client terminal indicative of the detected aberration.

In a further implementation form of the first, second, and third aspects, the at least one classifier is selected from the plurality of classifiers according to manual user input entered in a user interface associated with the client terminal.

In a further implementation form of the first, second, and third aspects, the at least one classifier is automatically selected from the plurality of classifiers according to a set-of-rules that analyze the indication of values of the plurality of current laboratory test results and select relevant classifiers.

In a further implementation form of the first, second, and third aspects, the method further comprises and/or the processor is further configured to and/or the computer program product includes additional instructions for storing the value of the at least one computed pathological indication in an electronic medical record (EMR) of the target individual.

In a further implementation form of the first, second, and third aspects, the value of the at least one computed pathological indication is presented as an entry of a report of the values of the plurality of current laboratory test.

In a further implementation form of the first, second, and third aspects, the value of the at least one computed pathological indication is indicative of early detection of cancer.

In a further implementation form of the first, second, and third aspects, the value of the at least one computed pathological indication is indicative of a prediction of liver disease based on current laboratory tests indicative of liver function.

In a further implementation form of the first, second, and third aspects, the value of the at least one computed pathological indication is indicative of a prediction of renal failure based on current laboratory tests indicative of renal function.

In a further implementation form of the first, second, and third aspects, the value of the at least one computed pathological indication is indicative of a diabetes monitoring score based on current laboratory tests indicative of adverse diabetic effects.

In a further implementation form of the first, second, and third aspects, the value of the at least one computed pathological indication is indicative of a prediction of rehospitalization.

In a further implementation form of the first, second, and third aspects, the value of the at least one computed pathological indication is indicative of sepsis.

In a further implementation form of the first, second, and third aspects, the value of the at least one computed pathological indication is indicative of organ specific deterioration, selected from the group consisting of: acute kidney injury (AKI), acute liver failure (ALF), and acute heart failure (AHF).

In a further implementation form of the second aspect, the computing device is in network communication with a laboratory information system (LIS) server over a laboratory network implementing a health level-7 (HL7) communication standard, wherein the LIS server is in communication with the at least one automated laboratory testing device and the at least one second automated laboratory testing device, wherein the indication of values of the plurality of current laboratory test results and the second indication of the second value of the at least one additional laboratory test result is received by the computing device from the LIS server, and the value of the at least one computed pathological indication is provided by the computing device to the LIS server.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

The present invention, in some embodiments thereof, relates to systems and methods for analyzing laboratory tests and, more specifically, but not exclusively, to systems and methods for enhancing laboratory testing.

An aspect of some embodiments of the present invention relates to systems, methods, and/or code instructions stored in a data storage device executable by one or more processors, for determining and automatically executing one or more other laboratory tests in addition to received multiple current laboratory test results obtained by one or more automated laboratory testing device(s) that automatically analyze a laboratory sample (e.g., blood, urine) of a target individual. The additional laboratory tests are performed by one or more other automated laboratory testing devices that automatically analyze at least a portion of the original laboratory sample of the target individual. One or more classifiers are selected according to the current laboratory test results. The additional laboratory tests are selected according to the selected classifiers and/or according to an analysis of the current laboratory test results. The selected classifier(s) are applied to the current laboratory test results and to the additional laboratory test result(s) to compute one or more computed pathological indications. Each computed pathological indication is an indication of a normal biological process (e.g., rehospitalization, risk of complications in an otherwise normal pregnancy in a low-risk woman) a pathogenic process (e.g., diabetes monitoring, early stage cancer, an indication of a prediction of liver disease, an indication of a prediction of a decrease in renal function, and an indication of an acute medical condition such as sepsis or acute kidney injury), and/or a pharmacological response to a therapeutic intervention (e.g., improvement in diabetic state in response to diabetic management and/or treatment with diabetic medications, risk of adverse side effects secondary to drug treatment).

Each computed pathological indication denotes an aggregated result of the multiple individual laboratory test results. The individual laboratory test results, each taken in isolation, may not necessarily be statistically significantly correlated with the computed pathological indication.

Optionally, one or more (e.g., each) of the laboratory test results is statistically insignificantly correlated with the evaluated clinical indication denoted by the computed pathological indication. When taken in isolation, one or more of the individual laboratory test result(s) cannot be used to infer the evaluated clinical indication denoted by the computed pathological indication. One or more of the individual test results may be irrelevant (e.g., to a clinician) when taken in isolation to try and arrive at the value of the computed pathological indication.

Such tests that may seem irrelevant and are omitted by the user (e.g., physician) that requested the original set of current laboratory tests are automatically added and executed as additional tests. For example, blood sodium may be ordered by the clinician suspecting diabetic ketoacidosis, but not necessarily by a family physician evaluating diabetic monitoring of a clinically stable patient. However, the value of the blood sodium concentration may be determined as being relevant as input by a classifier in computing a computed pathological indication indicative of the overall diabetic state of the patient, which may predict risk of complications in clinically stable patients. The blood sodium concentration test may be automatically added and executed in addition to the tests ordered by the family physician evaluating diabetic monitoring of the clinically stable patient.

Instructions for automatic execution of the additional laboratory test(s) are automatically generated based on an analysis of the set of current laboratory test results and/or in view of the selected classifier(s) that computes computed pathological indication(s) and/or in view of the selected computed pathological indication(s) (e.g., when the computed pathological indication(s) are manually requested by a user via a user interface of a client terminal). For example, when the classifier outputs a computed pathological indication indicative of a prediction of liver failure, and the set of blood tests results include AST (aspartate transaminase) and ALT (alanine transaminase), the PT/INR (prothrombin time, international normalized ratio) test may be automatically executed as another measure of liver function, which is processed by the classifier. The same laboratory sample (e.g., a portion thereof) may be used to perform the additional testing.

The additional test may be clinically irrelevant to the clinical indication when taken in isolation, but used by the classifier in evaluating the computed pathological indication. For example, blood sodium concentration may be irrelevant to the prediction of liver failure in isolation (e.g., would not necessarily be ordered by a clinician trying to predict liver failure in a patient that is clinically stable and not experiencing ascites) but may be automatically ordered to be evaluated by the classifier computing the computed pathological indication indicative of liver failure prediction.

Optionally, one or more patient parameters are obtained from an electronic medical record (EMR) of the patient. The EMR may be accessed directly, and/or via a clinical data repository (CDR) database. The patient parameters are obtained according to the selected classifier.

For example, when the classifier computes the computed pathological indication indicative of the prediction of liver failure, the amount of alcohol that the patient reportedly consumes is obtained from the EMR and used by the classifier to predict liver failure. In another example, the patient parameters include a change from the previous laboratory test result.

The classifier may analyze the trend in changes of laboratory tests results to obtain an indication of overall improvement or deterioration in the patient. For example, the individual laboratory tests results may be normal with an abnormal trend, or the individual laboratory tests results may be abnormal but with an improving trend. The additional patient parameters may be clinically irrelevant to the clinical indication when taken in isolation, but used by the classifier in evaluating the computed pathological indication.

The systems and/or methods and/or code instructions described herein provide a technical solution to the technical problem of analyzing multiple individual laboratory test results to obtain an overall indication of the patient. In particular, the technical problem relates to aggregating the multiple individual laboratory test results in an object manner to obtain an overall objective measure indicative of the state of the patient and/or predicting a future state of the patient.

For example, current liver function or a prediction of liver failure may be obtained by the following tests: AST, ALT, AST/ALT, aPTT, albumin, bilirubin (direct and indirect), history of alcohol consumption, history of use of hepatotoxic substances, and presence of ascites. The clinician subjectively and manually integrates the test results in their head based on clinical experience, to estimate the severity of liver injury.

Monitoring improvement or degradation in the condition of the patient by repeating the multiple tests is difficult and subjective. Moreover, analysis of multiple test results, in particular changes between values over tests conducted over multiple periods of time, is difficult. A situation that is especially challenging arises when the values of the test results fall within normal ranges, but a pattern of multiple tests results, and/or a trend and/or velocity in change of values over time may be indicative of the existence or developing medical problem that is otherwise hidden. Moreover, tests that would otherwise seem clinically irrelevant in isolation may not be requested by the clinician, for example, when the clinician is unable to appreciate the significant of the additional test in combination with the standard set of tests usually ordered for evaluation of the clinical indication.

The systems and/or methods and/or code instructions described herein utilize currently obtained laboratory sample(s) in the current round of automated laboratory tests to compute the computed pathological indication(s), which reduces or prevents additional future automated testing cycles that might otherwise arise, for example, by the treating physician ordering another set of tests that are performed during another round of automated testing. The testing efficiency of the automated laboratory testing equipment is improved.

The systems and/or methods and/or code instructions described herein generate new data in the form of the computed pathological indication(s), which may be presented as an additional entry in the report presenting the values of the laboratory tests, and/or may be stored in the EMR of the patient for future analysis and/or monitoring.

The systems and/or methods and/or code instructions described herein improve an underlying process within the technical field of laboratory information systems, in particular, within the field of automated laboratory testing.

The systems and/or methods and/or code instructions described herein do not simply describe the computation of the computed pathological indication(s) using a mathematical operation and receiving and storing data, but combine the acts of using outputs of automated laboratory testing device(s), generating instructions to perform additional laboratory test(s) using other automated laboratory testing device(s), and optionally patient medical data stored in EMRs hosted by a database stored on a data storage device, to aggregate individual laboratory testing results into a single objective metric. By this, the systems and/or methods and/or code instructions stored in a storage device executed by one or more processors described here go beyond the mere concept of simply retrieving and combining data using a computer.

The systems and/or methods and/or code instructions described herein are tied to physical real-life components, including one or more of: automated laboratory testing equipment, physical user interfaces (e.g., display), a data storage device storing patient data, and a hardware processor(s) that execute code instructions to compute the computed pathological indication(s).

Accordingly, the systems and/or methods and/or code instructions described herein are inextricably tied to computing technology and/or physical components to overcome an actual technical problem arising in laboratory information system management.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
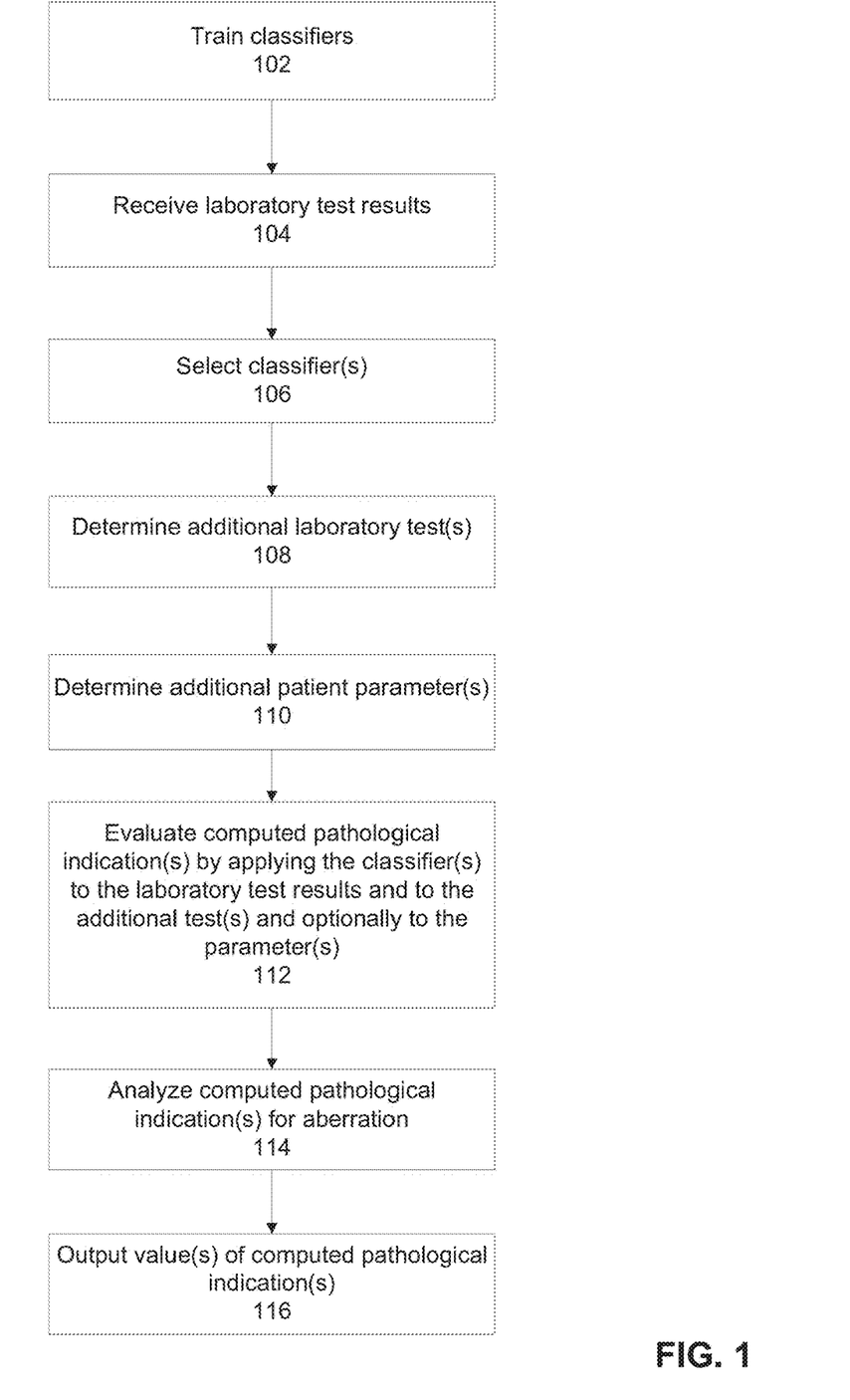
FIG. 1 is a flowchart of a method of computing computed pathological indication(s) based on current laboratory test results and additional determined laboratory test(s) results, in accordance with some embodiments of the present invention.
Figure 2:
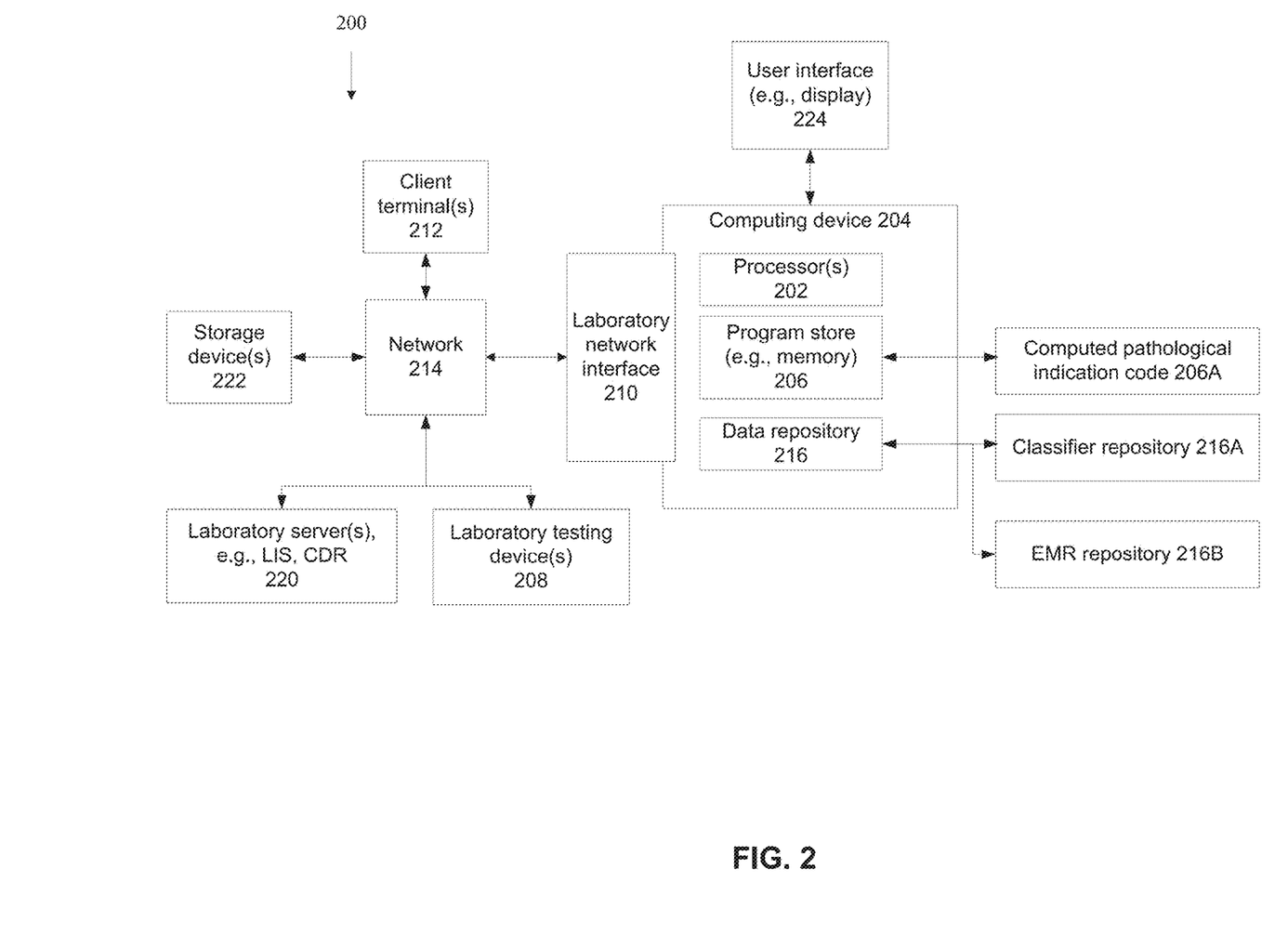
FIG. 2 is a block diagram of components of a system for computing the computed pathological indication(s) based on current laboratory test results and additional determined laboratory test(s) results, in accordance with some embodiments of the present invention.

Reference is now made to FIG. 1, which is a flowchart of a method of computing computed pathological indication(s) based on current laboratory test results and additional determined laboratory test(s) results, in accordance with some embodiments of the present invention. Reference is also made to FIG. 2, which is a block diagram of components of a system 200 for computing the computed pathological indication(s) based on current laboratory test results and additional determined laboratory test(s) results, in accordance with some embodiments of the present invention. System 200 may implement the acts of the method described with reference to FIG. 1, by processor(s) 202 of a computing device 204 executing code instructions stored in a program store 206.

Computing device 204 receives laboratory test results outputted by laboratory testing device(s) 208 that measure different substances in the laboratory sample and/or other characteristics, optionally in multiple samples, optionally quickly, and automatically (may include minimal human assistance), according to instructions code (e.g., compliant with laboratory information systems (LIS)). Exemplary laboratory testing devices 208 include: an automated complete blood count (CBC) analyzer, an automated urine analyzer machine, an automated coagulation analyzer, an automated biochemistry analyzer, an automated electrolyte analyzer, an automated blood gas analyzer, an automated blood glucose meter, and an automated cell imaging system.

Laboratory testing devices 208 may be connected using a laboratory network 214. The laboratory test results may be provided directly from laboratory testing devices 208 to computing device 204 (optionally via laboratory network 214 connected to a laboratory network interface 210 associated with computing device 204). The laboratory test results may be collected by laboratory information systems (LIS) server 220 (e.g., over laboratory network 214) from laboratory testing devices 208. Computing device 204 may be provided with the laboratory test results from LIS server 220. Computing device 204 receives the laboratory test results from laboratory testing device(s) 208 via one or more laboratory network interfaces 210, for example, a network interface, a wire connection, a wireless connection, other physical interface implementations, and/or virtual interfaces (e.g., software interface, application programming interface (API), software development kit (SDK)). Laboratory network interface 210 may implement a healthcare communication protocol, for example, health level-7 (HL7).

Computing device 204 may be integrated with an existing LIS server 220, for example, as a separate computing device that communicates with LIS server over a network and/or via a direct connection, as code instructions that are stored in a data storage device of the LIS server and executed by processor(s) of the LIS server, and/or as a hardware unit that is integrated with LIS server, for example a hardware card or chip that is plugged into the hardware of the LIS server.

Computing device 204 may be implemented as, for example, a client terminal, a server, software loaded on an existing LIS server, a computing cloud, a mobile device, a desktop computer, a thin client, a Smartphone, a Tablet computer, a laptop computer, a wearable computer, glasses computer, and a watch computer. Computing device 204 may include locally stored software that performs one or more of the acts described with reference to FIG. 1, and/or may act as one or more servers (e.g., network server, web server, a computing cloud) that provides services (e.g., one or more of the acts described with reference to FIG. 1) to one or more client terminals 212 over a network (optionally network 214), for example, providing software as a service (SaaS) to the client terminal(s) 212, providing an application for local download to the client terminal(s) 212, and/or providing functions via a remote access session to the client terminals 212, such as through a web browser and/or application stored on a Mobile device.

Client terminals 212 accessing computing device 204 may include one or more of: a server, a computing cloud, a mobile device, a desktop computer, a thin client, a Smartphone, a Tablet computer, a laptop computer, a wearable computer, glasses computer, and a watch computer. For example, a physician or patient accessing a report presenting the current laboratory test results and computed pathological indication(s).

Processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Storage device (also known herein as a program store, e.g., a memory) 206 stores code instructions implementable by processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 206 stores computed pathological indication code 206A that executes one or more acts of the method described with reference to FIG. 1.

Computing device 204 may include a data repository 216 for storing data, for example, a classifier repository 216A that stores the trained classifiers that compute the computed pathological indication(s), and EMR 216B that stores patient parameters processed by the classifiers in association with the current laboratory test results to compute the computed pathological indication(s). Data repository 216 may be implemented as, for example, a memory, a local hard-drive, a removable storage unit, an optical disk, a storage device, and/or as a remote server and/or computing cloud (e.g., accessed via a network connection).

Laboratory network interface 210 may be implemented as, for example, one or more of, a network interface card, a wireless interface to connect to a wireless network, a physical interface for connecting to a cable for network connectivity, a virtual interface implemented in software, network communication software providing higher layers of network connectivity, and/or other implementations. As used herein, the term network (e.g., network 214) may refer to, for example, the internet, a local area network, and a point to point connection with another computing device.

Computing device 204 may connect via laboratory network interface 210 to network 214 (and/or another communication channel, such as through a direct link (e.g., cable, wireless) and/or indirect link (e.g., via an intermediary computing unit such as a server, and/or via a storage device) with one or more of:

Client terminal(s) 212, for example, when the client terminal 212 is used by a physician to order laboratory tests and/or computed pathological indication(s), and/or used to view the results of the tests and/or computed pathological indication(s).

Server(s) 220 including the LIS server described herein.

Server(s) 220 including an EMR server and/or a CDR server that store and/or access patient medical data, for example, from the EMR of the patient. The CDR may be implemented as a real time database that consolidates data from a variety of clinical sources to present a unified view for each patient. The CDR is designed to retrieve data for each patient, rather than identifying a population of patients with common characteristics or to facilitate the management of a clinical department.

Patient parameters described herein may be obtained by computing device 204 from the EMR server and/or from CDR server.

Storage server 222 that stores the computed pathological indication(s), classifiers, and laboratory test results.

Computing device 204 and/or client terminal(s) 212 include and/or are in communication with a user interface 224 that includes a mechanism for a user to enter data (e.g., request for laboratory test and/or computed pathological indication(s)), and/or view presented data (e.g., the report including the results of the current laboratory tests, additional test results, and/or computed pathological indication(s)).

Exemplary user interfaces 224 include, for example, one or more of, a touchscreen, a display, a keyboard, a mouse, and voice activated software using speakers and microphone.

At 102, classifiers that each compute a respective computed pathological indication from a set of current laboratory test results are trained. The training may be performed by computing device 204 (or another computing device) based on medical history data obtained from electronic medical records of other patients. For example, a classifier that analyzes laboratory test results to determine whether early stage cancer is present is trained using historical laboratory tests obtained several years before a cancer diagnosis in patients. Alternatively or additionally, customized classifiers may be trained for each patient based on medical history data obtained from electronic medical records of the same patient.

For example, for patients with a history of frequency hospitalizations, a customized classifier that is indicative of the risk of re-hospitalization may be developed for the patient. The trained classifiers may be stored as code instructions in classifier repository 216A (e.g., database).

The computed pathological indication denotes an aggregation of the laboratory test results that provides an indication of a state of the patient. Exemplary computed pathological indications include: an indication of normal biological processes, an indication of a pathogenic processes, and an indication of pharmacological responses to a therapeutic intervention. The computed pathological indication(s) may denote the current state of the patient, for example, whether the patient is experiencing early stage cancer. The computed pathological indication(s) may denote a prediction of a risk of the patient for developing a medical problem.

The training may be performed using the historical laboratory test results as desired input, and values of the computed pathological indication which denote the output of the classifier.

The values of the computed pathological indication may be, for example, manually denoted by a user (e.g., a scale indicating severity of liver disease with values manually defined by a physician), obtained from the electronic medical record of the patient (e.g., a value of a validated scale of severity of liver disease entered by a physician), and/or automatically identified by code instructions (e.g., code that analyzes hospital admission records to determine hospital admission and length of stay).

The training may be performed using one or more machine learning methods, for example, K-Nearest neighbors (KNN), random forest, weighted linear regression, neural network, decision trees, and Bayes. The training may be based on supervised learning (e.g., where the user defines the outcome), and/or unsupervised learning (e.g., where code automatically identifies the outcome).

Exemplary computed pathological indications and the laboratory tests they are computed from include:

A computed pathological indication indicative of early detection of cancer, based on blood tests, physical exam findings, and radiological findings.

Another computed pathological indication indicative of a prediction of liver disease based on current laboratory tests indicative of liver function.

Yet another computed pathological indication indicative of a prediction of renal failure based on current laboratory tests indicative of renal function.

Yet another computed pathological indication indicative of a diabetes monitoring score based on current laboratory tests and physical examination findings indicative of adverse diabetic effects.

Yet another computed pathological indication indicative of a prediction of rehospitalization based on current laboratory tests.

Yet another computed pathological indication indicative of sepsis based on current laboratory tests.

Yet another computed pathological indication indicative of organ specific deterioration, including one or more of: acute kidney injury (AKI), acute liver failure (ALF), and acute heart failure (AHF).

At 104, an indication of values of current laboratory test results is obtained by computing device 204. The values of current laboratory test results may be transmitted to computing device 204 by LIS server 220. The measurements are performed by one or more laboratory testing devices 208 that automatically analyze laboratory sample(s) collected from a target individual. The values of the current laboratory test results may be computed from the measurements by the respective laboratory testing device 208 that performed the measurement, and/or the values may be computed by LIS server 220 according to the measurements performed by laboratory testing device(s) 208.

The current laboratory tests may be ordered by the treating physician, for example, in an inpatient and/or outpatient setting. The current laboratory tests may be ordered using a user interface, for example, a graphical user interface in which the user selects and/or enters the desired tests. The request for the laboratory tests may be transmitted to the LIS server. The LIS server may receive multiple requests for laboratory tests from multiple users, organize the requests, and transmit instructions to perform the tests according to the organized request to the relevant automated laboratory testing devices. The automated laboratory testing devices may report the test results to the LIS server.

At 106, one or more classifiers are selected from the available classifiers (e.g., stored in classifier repository 216A). The classifiers are selected according to an analysis of the indication of values of the current laboratory test results. Optionally, one or more computed pathological indications are selected. The classifiers corresponding to the selected computed pathological indications are selected.

It is noted that different classifiers may be selected for different result values of the same laboratory test. For example, for a set of complete blood count tests with a first set of result values a first classifier is selected that computes a first computed pathological indication. For the same complete blood count tests with another set of result values a second classifier is selected that computes a second computed pathological indication which is different than the first computed pathological indication computed by the first classifier.

Optionally, the classifier(s) is selected according to manual user input, for example, entered in a user interface associated with client terminal 212 in network communication with computing device 204. The manual user input may be indicative of a user request for computation of one or more certain computed pathological indications. For example, the physician ordering the blood test results may select the computed pathological indication indicative of adverse effects of a medication the patient is taking.

Alternatively or additionally, the classifier is automatically selected according to a set-of-rules that analyzes the indication of the current laboratory test results. The classifier selection may be programmed as a reflex test defined by a set-of-rules in code instructions executed by the LIS server. The set-of-rules are evaluated according to the indication of the current laboratory test results to identify one or more reflex tests (e.g., the associated set-of-rules is evaluated as TRUE).

Each reflex test maps to one or more classifiers. For example, when the current laboratory test results include a set of liver function tests, the classifier that computes the computed pathological indication indicative of a prediction of liver failure may be automatically selected. In another example, the classifier that computes the computed pathological indication indicative of early stage cancer may be selected by default for each set of ordered laboratory tests, to screen all patients for early cancer.

Alternatively or additionally, the classifier is automatically selected according to a set-of-rules that analyzes the patient medical records. For example, for patients with a personal or family history of cancer, the classifier that computes the computed pathological indication indicative of early onset of cancer may be automatically selected.

At 108, an analysis of the indication of values of the current laboratory test results determines one or more additional laboratory tests for application of the selected classifier. The analysis is performed in view of the selected classifier. For example, when the classifier that computes the computed pathological indication indicative of risk of hospitalization is selected, and liver function tests have been performed, additional renal function tests may be determined for application of the classifier to computer the computed pathological indication.

The additional laboratory tests may be defined by a mapping and/or set-of-rules that define which laboratory tests are used as input for the selected classifier. The laboratory tests required for input into the classifier may be compared to the current laboratory test results to determine the missing tests. The additional tests are defined according to the missing tests. Alternatively or additionally, the selected classifier and the current laboratory test results are applied to another trained machine learning code instructions which output the additional laboratory tests that are required for application of the classifier.

The additional test based on the analysis may include tests that would not traditionally be ordered by clinicians when the original set of laboratory tests is ordered, and/or may include tests that are not statistically significantly correlated with the clinical scenario the user is attempting to evaluate.

For example, when the computed pathological indication indicative of the overall diabetic state of the patient is ordered, along with traditional diabetic associated blood test, such as fasting blood glucose level, and hemoglobin HbA1c, the additional test based on the analysis may include blood sodium (and/or other electrolytes) which would not normally be ordered by the clinician for monitoring of diabetes mellitus (unless specific syndromes are suspected, for example, diabetic ketoacidosis). The additional test may be used to evaluate the overall diabetic state of the patient, which may include a risk of complications, for example, a risk of future diabetic ketoacidosis.

Computing device 204 may automatically generate instructions, and/or transmit a message to LIS server 220 to automatically generate the instructions, for automatic execution of another (e.g., second, third, or greater) set of laboratory tests by another automatic laboratory testing device 208.

The other automatic laboratory testing device may execute the laboratory tests on the same laboratory sample (or portion thereof) to obtain an indication of a value of the additional laboratory test.

For example, a portion of the blood sample of the target patient may be automatically extracted and sent to the other laboratory testing device for execution of the additional set of laboratory tests. For example, when the original set of blood tests include a complete blood count, and the selected classifier requires tests results of blood coagulation tests, a portion of the blood may be removed and sent to the device that measures coagulation.

Alternatively or additionally, the classifier is selected (e.g., as described with reference to act 106) when the request for the sample from the target individual is requested, before the sample is acquired (e.g., by a nurse at a lab). Additional samples may be automatically added to the original sample request based on the additional determined laboratory tests according to the selected classifier. For example, when a blood test is ordered and a certain classifier is selected, laboratory tests that require a urine sample may be determined.

The instructions to the nurse may include instructions to obtain both a blood and a urine sample. Alternatively or additionally, a robot processing the laboratory sample may divide the laboratory sample according to the additional tests to ensure sufficient sample is available for testing by multiple devices.

At 110, an analysis of the indication of values of the current laboratory test results may determine that one or more additional patient parameter of the target individual are to be obtained for application of the selected classifier.

For example, for the classifier that computes the computed pathological indication indicative of risk of rehospitalization, the value of the number of previous rehospitalizations and/or comorbidities of the patient and/or the age of the patient may be determined as to be obtained for processing by the classifier. For example, for the classifier that computes the computed pathological indication indicative of a return to normal biological functioning, the value of the previous laboratory tests may be determined as to be obtained for processing by the classifier.

The additional patient parameters may include manually performed clinical evaluations, which may be obtained for example from EMR 216B of the target individual and/or upon request from a physician (and/or other user) using a user interface (e.g., presented on a screen of a client terminal. For example, results of a fundoscopic exam performed by an ophthalmologist, nerve function tests performed by a neurologist, and physical exam findings performed by a family physician.

A clinical data repository database (e.g., hosted by server 220 and/or EMR 216B) may be automatically accessed by computing device 204 to obtain the indication of the value of determined patient parameter of the target individual. Computing device 204 may access EMR 216B directly, or use CDR as an interface for accessing EMR 216B, for example, using the Fast Healthcare Interoperability Resources (FHIR) protocol accessed using an interface (e.g., application programming interface (API)).

Exemplary patient parameters include: a previous measurement of one or more of the current laboratory test results, a demographic parameter, a medical diagnosis, a smoking parameter, a medication use parameter, a family history parameter, a genetic parameter, a medical history parameter, and a physical exam finding parameter.

Optionally, a change in the value of one or more of the current laboratory test results and one or more previous values of the current laboratory test results is computed. A trend may be computed.

At 112, one or more computed pathological indications are evaluated by applying the selected classifier(s) to the indication of values of current laboratory test results and to the additional laboratory test results. The evaluation of the computed pathological indication by applying the classifier may be performed by computing device 204, optionally in response to request instructions received from LIS server 220. The value of the evaluated computed pathological indication may be transmitted to LIS server 220.

Each classifier may be applied to a different subset of laboratory tests results and to the respective additional laboratory rest result, as defined by the respective classifier. The classifier(s) may be further applied to the additional patient parameter(s), and/or to the computed changes in value(s) of the current laboratory test result(s).

At 114, the value of the respective computed pathological indication(s) may be analyzed according to a set-of-rules, in view of the indication of values of the current laboratory test results, to detect an aberration from an expected value of the computed pathological indication(s). For example, for a healthy young woman performing laboratory testing as a routine pregnancy screen, a computed pathological indication indicative of risk of liver failure may be a detected aberration. The analysis may be performed, for example, by LIS server 220, by code executing on the client terminal of the user that issued the original request for the current laboratory tests, by computing device 204, and/or by the other computing devices.

The aberrations may be flagged and presented on a display of a client terminal, for example, to the requesting physician and/or to an administrator. For example, the physician may choose to further explore the aberration as having potentially uncovered a hidden risk, or choose to ignore the aberration. Aberrations may trigger additional training of the classifier to improve relevancy of the results.

At 116, the evaluated value of the computed pathological indication(s) are provided for presentation, for example, on a display of client terminal 212. The value of the computed pathological indication(s) may be presented as an entry of a report of the values of the current laboratory test(s).

The evaluated value of the computed pathological indication(s) may be transmitted to a remote server and/or stored in the EMR of the target individual, for example using HL7 to transmit to the EMR server and/or the CDR server interfacing with the data storage device storing the EMR.

The set of stored evaluated values of the computed pathological indication(s) may be monitored for trends and/or changes by code instructions. For example, the computed pathological indication indicative of diabetes monitoring may be tracked to determine whether the diabetes monitoring of the patient is improving or deteriorating. The monitoring may be performed by code instructions stored in association with the EMR, by computing device 204, and/or hosted by a remote server 220.

Figure 3:
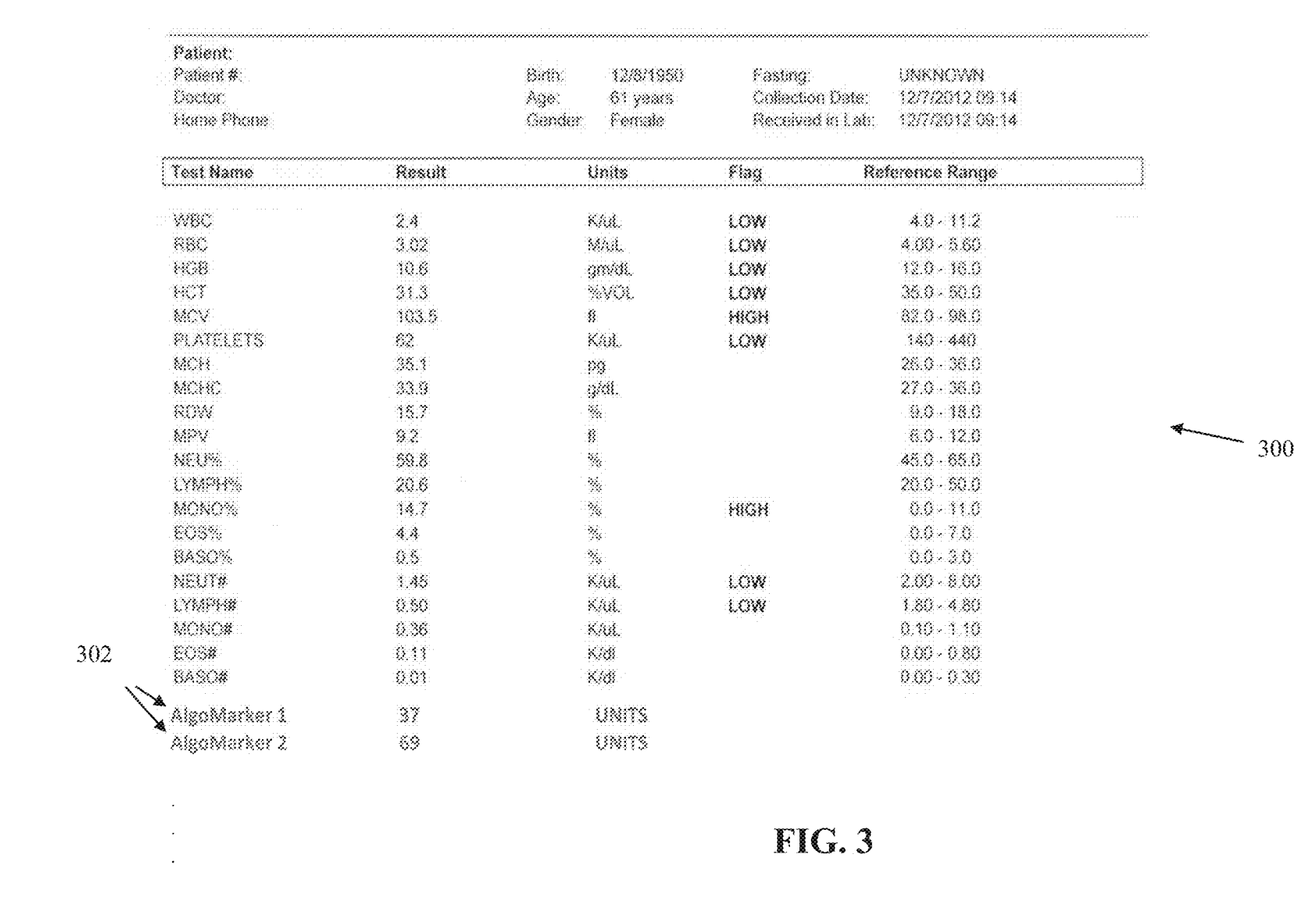
FIG. 3 is a schematic of an exemplary enhanced report presenting results of evaluated computed pathological indication(s), in accordance with some embodiments of the present invention.

Reference is now made to FIG. 3, which includes an exemplary enhanced report 300 presenting results of evaluated computed pathological indication(s), in accordance with some embodiments of the present invention. Enhanced report 300 includes entries of results of the standard laboratory tests that were performed, and includes entries of values of computed pathological indications 302 computed by applying classifiers to subsets of the standard laboratory tests, as described herein. The values of computed pathological indications 302 may be used, for example, by the physician as an aid in assessing an aggregation of the laboratory test results presented in report 300.

Figure 4:
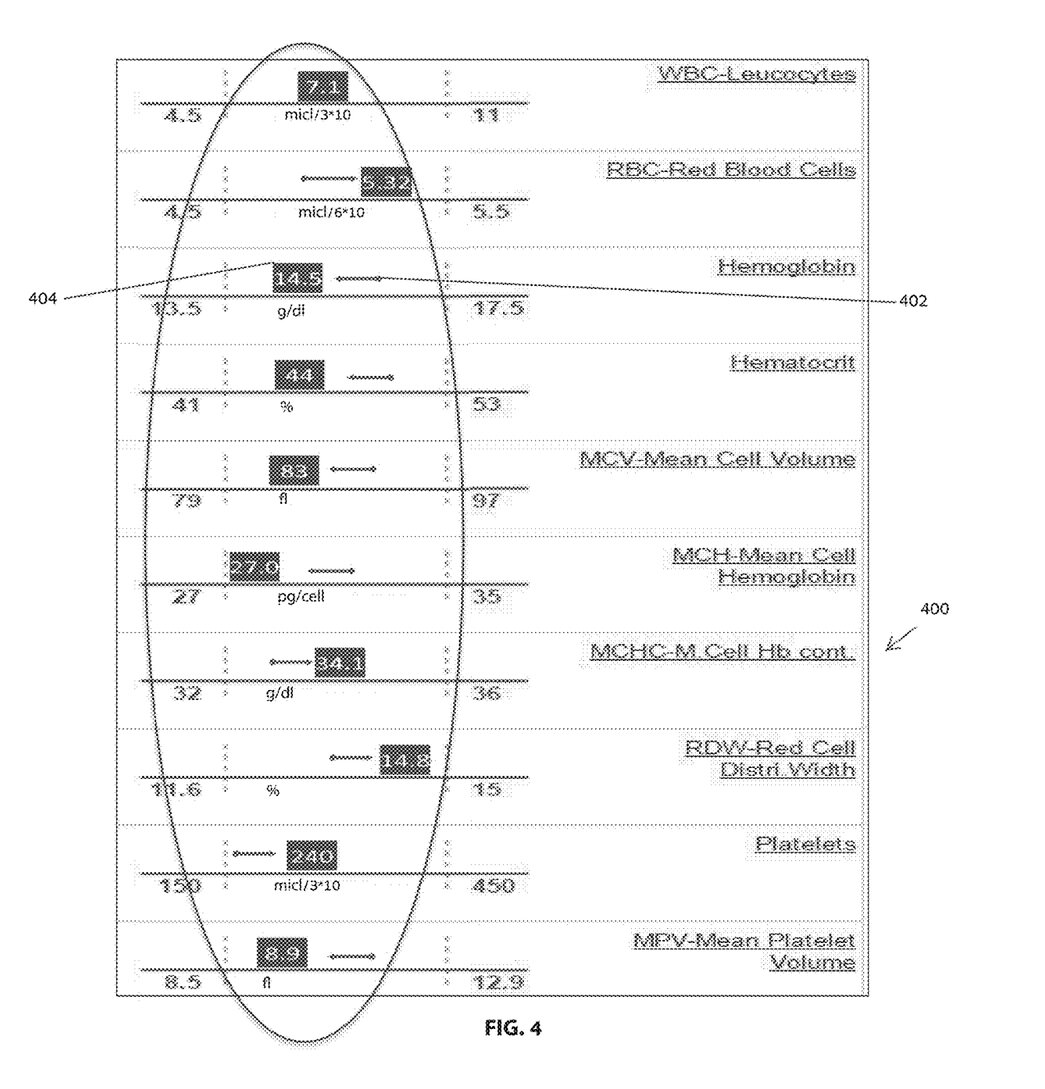
FIG. 4 is a schematic depicting a scenario in which computation of the computed pathological indication suggests a medical problem that might otherwise remain hidden, in accordance with some embodiments of the present invention.

Reference is now made to FIG. 4, which is a schematic depicting a scenario in which computation of the computed pathological indication suggests a medical problem that might otherwise remain hidden, in accordance with some embodiments of the present invention. Report 400 depicts results of laboratory blood tests values, with indications between values of a previous set of tests conducted during an earlier time period, and the current test values. The origin of the arrow shows as a dot (element 402 points to one example) denotes the previous value of the test.

The cube (element 404 points to one example) denotes the current value of the test. It is noted that all of the current and previous blood test values fall within the range of normal. The computed pathological indication, which may be computed based on the changes in the values of the blood tests, may be indicative of a developing medical condition, or an underlying medical condition which has not yet manifest itself.

Figure 5:
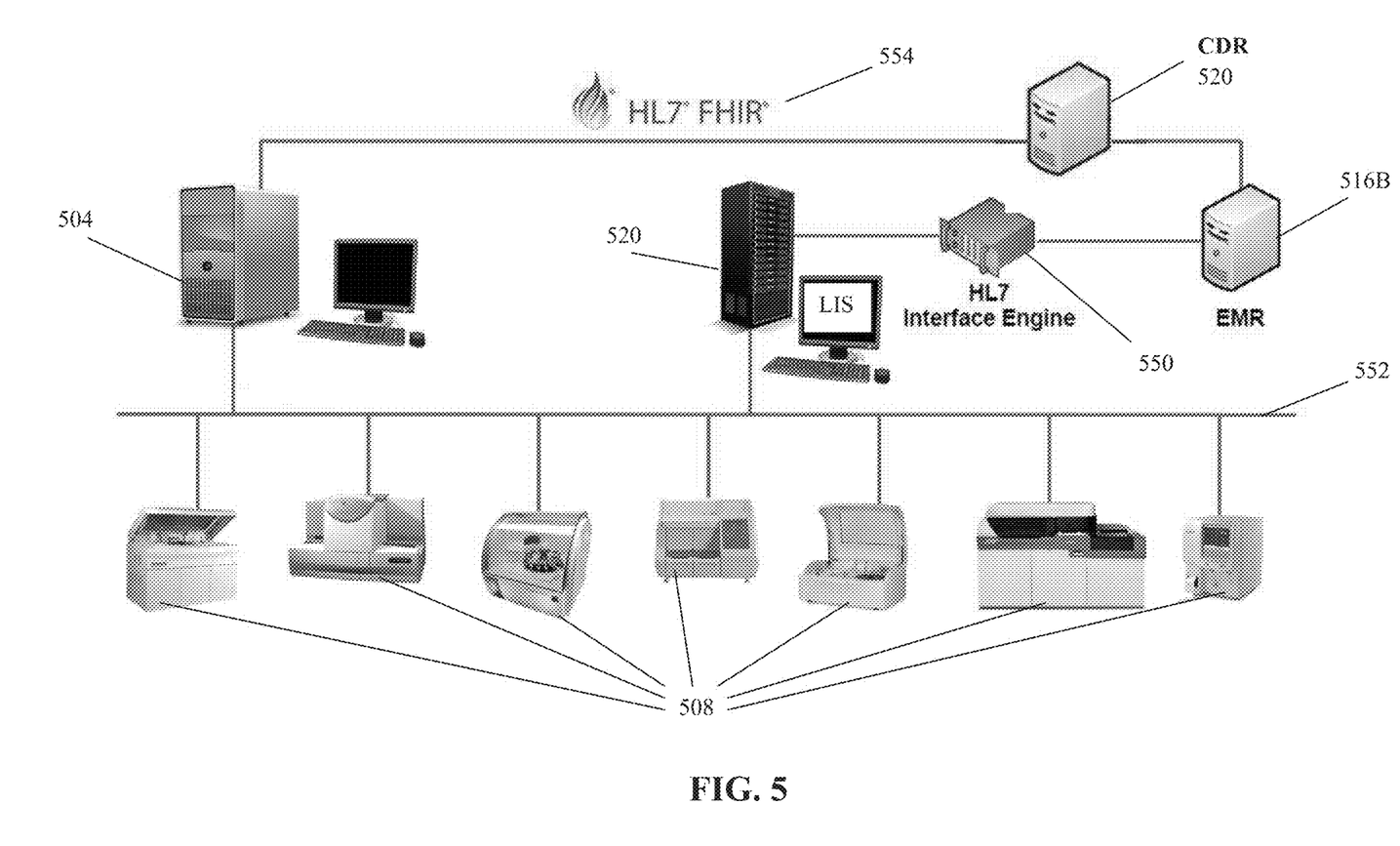
FIG. 5 is a schematic of an exemplary architecture that computes computed pathological indication(s), in accordance with some embodiments of the present invention.

Reference is now made to FIG. 5, which is a schematic of an exemplary architecture 500 that computes computed pathological indication(s) based on one or more components of system 200 described with reference to FIG. 2, in accordance with some embodiments of the present invention. Computing device 504 corresponds to computing device 204. LIS server 520 corresponds to LIS implementation of server 220. EMR 516B may be stored on a server and/or external storage device, corresponding to EMR repository 216B. Automated laboratory testing devices 508 correspond to automated laboratory testing devices 208. HL7 interface engine 550 provides communication between LIS server 520 and EMR server and/or storage device 516B. It is noted that other communication protocols may be used.

A laboratory network 552 (which may correspond to laboratory network, laboratory network interface 210, and/or network 214 described with reference to FIG. 2) provides communication between computing device 504 and LIS 520. Laboratory network 552 may be implemented as, for example, a local laboratory network, the internet, direct cables, short range wireless communication, and/or other implementations.

LIS server 520 is in communication with automated laboratory devices 508 optionally over laboratory network 552. LIS server 520 transmits instructions to automated laboratory devices 508 to perform the requested current laboratory tests and the additional laboratory tests on the laboratory sample obtained from the target patient, and receives the results of the executed tests. The results are provided to computing device 504.

Computing device 504 connects to laboratory network 552 using a LIS compliant communication protocol.

Computing device 504 may connect to EMR 516B using a dedicated communication protocol 554, for example, FHIR, or other suitable communication standards. Alternatively, computing device 504 is connected to a CDR server 520 using a dedicated communication protocol (e.g., FHIR).

CDR 520 communicates with EMR 516B acting as an interface to EMR 516B for computing device 504.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant laboratory information system computing devices and automated laboratory testing devices will be developed and the scope of the terms laboratory information system computing devices and automated laboratory testing devices are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for providing a client terminal with a numerical value of at least one target pathological indication in response to an indication of current laboratory test results of a patient, comprising:

a non-transitory memory having stored thereon a code for execution by at least one hardware processor of a computing device associated with a database storing a plurality of classifiers and associated with at least one automated laboratory testing device via a network, the code comprising:

code for receiving an indication of values of a plurality of current laboratory test results calculated based on an automated analysis of at least one laboratory sample collected from a target individual;

code for receiving at least one additional patient parameter;

code for selecting at least one classifier from the plurality of classifiers according to at least one target pathological indication obtainable from the indication of values of the plurality of current laboratory test results, wherein each of the plurality of classifiers is trained on a respective training dataset to output a respective different pathological indication, the respective training dataset including, for each of a plurality of sample individuals, a plurality of historical laboratory test results, the at least one additional patient parameter, and a corresponding numerical value of the respective pathological indication denoting an aggregation of the historical laboratory test results indicative of a state of the respective sample individual;

code for determining at least one additional laboratory test according to tests missing from the plurality of current laboratory tests for input into the selected at least one classifier;

code for automatically sending a control signals to the at least one second automatic laboratory testing device to perform the at least one additional laboratory test selected from a group consisting of: liver function test, renal function test, diabetic associated test, complete blood count (CBC), blood coagulation test, urinalysis, biochemistry test, electrolyte test, blood gas test, blood glucose level, and cell analysis, the at least one additional test performed on blood and/or urine comprising at least a portion of the at least one laboratory sample collected from the target individual to obtain a second indication of a second value of the at least one additional laboratory test, when the determining indicates that the at least one additional laboratory test is missing from the plurality of current laboratory tests and that the at least one additional laboratory test is for input into the selected at least one classifier;

code for evaluating a numerical value of a plurality of candidate numerical values of the at least one target pathological indication by applying the selected at least one classifier to the indication of values of the plurality of current laboratory test results, the second indication of the second value of the at least one additional laboratory test result, and to the at least one additional patient parameter, wherein the numerical value of the target pathological indication is indicative of a state of the patient, and denotes an aggregation of the plurality of current laboratory test results, the second indication of the second value of the at least one additional laboratory test result, and the at least one additional patient parameter; and code for outputting the numerical value of the at least one target pathological indication for presentation by the client terminal.

2. The system of claim 1, wherein the computing device is in network communication with a laboratory information system (LIS) server over a laboratory network implementing a health level-7 (HL7) communication standard, wherein the LIS server is in communication with the at least one automated laboratory testing device and the at least one second automated laboratory testing device, wherein the indication of values of the plurality of current laboratory test results and the second indication of the second value of the at least one additional laboratory test result is received by the computing device from the LIS server, and the value of the at least one target pathological indication is provided by the computing device to the LIS server.

3. A computer program product for providing a client terminal with a numerical value of at least one target pathological indication in response to an indication of current laboratory test results of a patient, comprising:

a non-transitory memory having stored thereon a code for execution by at least one hardware processor of a computing device associated with a database storing a plurality of classifiers and associated with at least one automated laboratory testing device via a network, the code comprising:

instructions for receiving an indication of values of a plurality of current laboratory test results calculated based on an automated analysis of at least one laboratory sample collected from a target individual;

instructions for receiving at least one additional patient parameter;

instructions for selecting at least one classifier from the plurality of classifiers according to at least one target pathological indication obtainable from the indication of values of the plurality of current laboratory test results, wherein each of the plurality of classifiers is trained on a respective training dataset to output a respective different pathological indication, the respective training dataset including, for each of a plurality of sample individuals, a plurality of historical laboratory test results, the at least one additional patient parameter, and a corresponding numerical value of the respective pathological indication denoting an aggregation of the historical laboratory test results indicative of a state of the respective sample individual;

instructions for determining at least one additional laboratory test according to tests missing from the plurality of current laboratory tests for input into the selected at least one classifier;

instructions for automatically sending a control signals to the at least one second automatic laboratory testing device to perform the at least one additional laboratory test selected from a group consisting of: liver function test, renal function test, diabetic associated test, complete blood count (CBC), blood coagulation test, urinalysis, biochemistry test, electrolyte test, blood gas test, blood glucose level, and cell analysis, the at least one additional test performed on blood and/or urine comprising at least a portion of the at least one laboratory sample collected from the target individual to obtain a second indication of a second value of the at least one additional laboratory test, when the determining indicates that the at least one additional laboratory test is missing from the plurality of current laboratory tests and that the at least one additional laboratory test is for input into the selected at least one classifier;

instructions for evaluating a numerical value of a plurality of candidate numerical values of the at least one target pathological indication by applying the selected at least one classifier to the indication of values of the plurality of current laboratory test results, the second indication of the second value of the at least one additional laboratory test result, and the at least one additional patient parameter, wherein the numerical value of the target pathological indication is indicative of a state of the patient, and denotes an aggregation of the plurality of current laboratory test results, the second indication of the second value of the at least one additional laboratory test result, and the at least one additional patient parameter; and instructions for outputting the numerical value of the at least one target pathological indication for presentation by the client terminal.

4. A method of providing a client terminal with a numerical value of at least one target pathological indication in response to an indication of current laboratory test results of a patient, comprising:

receiving by a computing system associated with a database storing a plurality of classifiers, from at least one automated laboratory testing device and via a network, an indication of values of a plurality of current laboratory test results calculated based on an automated analysis of at least one laboratory sample collected from a target individual;

receiving at least one additional patient parameter;

selecting at least one classifier from the plurality of classifiers according to at least one target pathological indication obtainable from the indication of values of the plurality of current laboratory test results, wherein each of the plurality of classifiers is trained on a respective training dataset to output a respective different pathological indication, the respective training dataset including, for each of a plurality of sample individuals, the least one additional patient parameter, a plurality of historical laboratory test results and a corresponding numerical value of the respective pathological indication denoting an aggregation of the historical laboratory test results indicative of a state of the respective sample individual;

determining at least one additional laboratory test according to tests missing from the plurality of current laboratory tests for input into the selected at least one classifier;

automatically sending a control signal to the at least one second automatic laboratory testing device to perform the at least one additional laboratory test selected from a group consisting of: liver function test, renal function test, diabetic associated test, complete blood count (CBC), blood coagulation test, urinalysis, biochemistry test, electrolyte test, blood gas test, blood glucose level, and cell analysis, the at least one additional test performed on blood and/or urine comprising at least a portion of the at least one laboratory sample collected from the target individual to obtain a second indication of a second value of the at least one additional laboratory test, when the determining indicates that the at least one additional laboratory test is missing from the plurality of current laboratory tests and that the at least one additional laboratory test is for input into the selected at least one classifier;

evaluating a numerical value of a plurality of candidate numerical values of the at least one target pathological indication by applying the selected at least one classifier to the indication of values of the plurality of current laboratory test results, to the second indication of the second value of the at least one additional laboratory test result, and to the at least one additional patient parameter, wherein the numerical value of the target pathological indication is indicative of a state of the patient, and denotes the aggregation of the plurality of current laboratory test results, the second indication of the second value of the at least one additional laboratory test result, and the at least one additional patient parameter; and outputting the numerical value of the at least one target pathological indication for presentation by the client terminal.

5. The method according to claim 4, wherein the at least one additional laboratory test is not included in the plurality of current laboratory tests received in an originating request from a user.

6. The method according to claim 4, wherein each of the plurality of classifiers computes a respective target pathological indication from a subset of current laboratory test results to generate a clinical indication of at least one of: normal biological processes, pathogenic processes, and pharmacological responses to a therapeutic intervention.

7. The method according to claim 4, wherein at least one member of the subset of current laboratory test results is statistically insignificantly correlated with the clinical indication denoted by the evaluated at least one target pathological indication.

8. The method according to claim 4, further comprising:

determining according to an analysis of the indication of values of the plurality of current laboratory test results, at least one additional patient parameter of the target individual for application of the selected at least one classifier;

accessing a clinical data repository database to obtain an indication of a value of at least one additional patient parameter of the target individual; and applying the selected at least one classifier to the indication of the values of the plurality of current laboratory test results and the at least one additional patient parameter.

9. The method according to claim 8, wherein the at least one additional patient parameter is selected from the group consisting of: a previous measurement of at least one of the plurality of current laboratory test results, a demographic parameter, a medical diagnosis, a smoking parameter, a medication use parameter, a family history parameter, a genetic parameter, a medical history parameter, and a physical exam finding parameter.

10. The method according to claim 8, further comprising computing a change in the value of at least one of the plurality of current laboratory test results and at least one previous value of the at least one of the plurality of current laboratory test results, and applying the selected at least one classifier to the computed change in the value.

11. The method according to claim 4, further comprising analyzing the value of the at least one target pathological indication according to a set-of-rules in view of the indication of values of the plurality of current laboratory test results to detect an aberration from an expected value of the at least one target pathological indication, and generating an alert on a client terminal indicative of the detected aberration.

12. The method according to claim 4, wherein the at least one classifier is selected from the plurality of classifiers according to manual user input entered in a user interface associated with the client terminal.

13. The method according to claim 4, wherein the at least one classifier is automatically selected from the plurality of classifiers according to a set-of-rules that analyze the indication of values of the plurality of current laboratory test results and select relevant classifiers.

14. The method according to claim 4, further comprising storing the value of the at least one target pathological indication in an electronic medical record (EMR) of the target individual.

15. The method according to claim 4, wherein the value of the at least one target pathological indication is presented as an entry of a report of the values of the plurality of current laboratory test.

16. The method according to claim 4, wherein the value of the at least one target pathological indication is indicative of early detection of cancer.

17. The method according to claim 4, wherein the value of the at least one target pathological indication is indicative of a prediction of liver disease based on current laboratory tests indicative of liver function.

18. The method according to claim 4, wherein the value of the at least one target pathological indication is indicative of a prediction of renal failure based on current laboratory tests indicative of renal function.

19. The method according to claim 4, wherein the value of the at least one target pathological indication is indicative of a diabetes monitoring score based on current laboratory tests indicative of adverse diabetic effects.

20. The method according to claim 4, wherein the value of the at least one target pathological indication is indicative of a prediction of rehospitalization.

21. The method according to claim 4, wherein the value of the at least one target pathological indication is indicative of sepsis.

22. The method according to claim 4, wherein the value of the at least one target pathological indication is indicative of organ specific deterioration, selected from the group consisting of: acute kidney injury (AKI), acute liver failure (ALF), and acute heart failure (AHF).

23. The method according to claim 4, further comprising:
   training each of the plurality of classifiers on the respective training dataset to output the respective different pathological indication, the respective training dataset including, for each of the plurality of sample individuals, the plurality of historical laboratory test results and the corresponding numerical value of the respective pathological indication denoting the aggregation of the historical laboratory test results indicative of the state of the respective sample individual.

24. The method of claim 4, further comprising, iteratively computing over a time interval a plurality of values of the at least one pathological indication using iteratively obtained plurality of current laboratory test results from respective iteratively collected laboratory samples, computing a trend of the plurality of values over the time interval, and monitoring the trend for changes to determine an improvement or deterioration.

25. The method of claim 4, wherein the at least one additional patient parameter is selected from the group consisting of: a demographic parameter, a medical diagnosis, a smoking parameter, a medication use parameter, a family history parameter, a genetic parameter, a medical history parameter, and a physical exam finding parameter.

26. The method of claim 4, wherein the at least one additional patient parameter is obtained in response to additional patient data that is missing for input into the selected at least one classifier with the plurality of current laboratory tests.

27. The method of claim 4, wherein the at least one second automatic laboratory testing device is selected from a group consisting of: an automated complete blood count (CBC) analyzer, an automated urine analyzer machine, an automated coagulation analyzer, an automated biochemistry analyzer, an automated electrolyte analyzer, an automated blood gas analyzer, an automated blood glucose meter, and an automated cell imaging system.

* * * * *